United States Patent [19]
Montesanto et al.

[11] Patent Number: 5,970,168
[45] Date of Patent: Oct. 19, 1999

[54] FOURIER FILTERING MECHANISM FOR INSPECTING WAFERS

[75] Inventors: Steve Montesanto, San Jose; Gershon Perelman, Cupertino; Rudolf Brunner, Sunnyvale, all of Calif.

[73] Assignee: KLA-Tencor Corporation, San Jose, Calif.

[21] Appl. No.: 08/906,021

[22] Filed: Aug. 5, 1997

[51] Int. Cl.⁶ .................................................. G06K 9/00
[52] U.S. Cl. .................... 382/149; 382/210; 250/347; 250/390.09; 378/145; 378/154; 378/155
[58] Field of Search .................... 378/154, 155; 382/143, 144, 145, 147, 149, 150, 151, 280, 283; 250/347, 390.07, 237 G; 359/558, 559

[56] References Cited

U.S. PATENT DOCUMENTS

| | | | |
|---|---|---|---|
| 3,620,598 | 11/1971 | Gerald | 359/559 |
| 4,340,818 | 7/1982 | Barnes | 378/155 |
| 4,465,371 | 8/1984 | Pernick | 359/558 |
| 4,648,041 | 3/1987 | Tarr | 324/228 |
| 5,274,434 | 12/1993 | Morioka et al. | 356/237 |
| 5,276,498 | 1/1994 | Galbraith et al. | 356/237 |
| 5,425,816 | 6/1995 | Cavicchi et al. | 438/98 |
| 5,463,459 | 10/1995 | Morioka et al. | 356/237 |
| 5,806,181 | 9/1998 | Khandros et al. | 29/874 |

*Primary Examiner*—Christopher S. Kelley
*Assistant Examiner*—Sheela Chawan
*Attorney, Agent, or Firm*—Carr & Ferrell LLP

[57] ABSTRACT

The present invention resides in a Fourier filter to detect defects on semiconductor wafers. The present invention relates to a Fourier filter to detect defects on semiconductor wafers which is less susceptible to having the filter output affected by vibrations and which avoids the physical contact from conventional damping.

21 Claims, 9 Drawing Sheets

FOURIER FILTERING MECHANISM FOR INSPECTING WAFERS

BACKGROUND OF THE INVENTION

1. Field of the Invention

The present invention relates generally to inspection of semiconductor devices being fabricated, and more particularly to a Fourier filter for detecting defects in repetitive features on semiconductor wafers.

2. Description of the Background Art

Known methods exist to make inspection instruments for detecting defects on semiconductor wafers. These inspection instruments normally detect defects using some means to filter out the desired patterning on the semi-conductor wafers. There are optical filter implementations in the prior art, such as a liquid crystal display (LCD)-based filter and a photographic-based filter, that have been used in inspection instruments. U.S. Pat. No. 5,537,669 to Evans et al. describes another method and apparatus for the inspection of random or repeating patterns using a hybrid of spatial domains and frequency domain, i.e., "Fourier-like" transforms. These prior art filtering implementations have various disadvantages such as optical distortion, poor contrast, and process complexity.

The basis for defect detection takes advantage of the repetitive nature of the patterning on wafers to compare images of nominally identical features, with differences being identified as defects. In general, wafer patterns are repetitive on two scales: on the coarse scale, a single die or functional device is repeated many times across the wafer; these dies will later be separated and packaged separately. Dice are typically between 4 and 25 mm on a side, and rectangular in shape. On the fine scale, many devices have repetitive geometries within a die, such as an array of memory cells, where the repeating pattern has a period of several microns ($\mu$m.), typically 2 to 20 $\mu$m. This array area is where a Fourier filter can be of particular utility.

When an array on a wafer die is illuminated with coherent, collimated light to detect defects, the array serves as a reflective diffraction grating that produces diffraction spots which can be seen clearly in the pupil (Fourier) plane of an imaging system.

Figure 1:
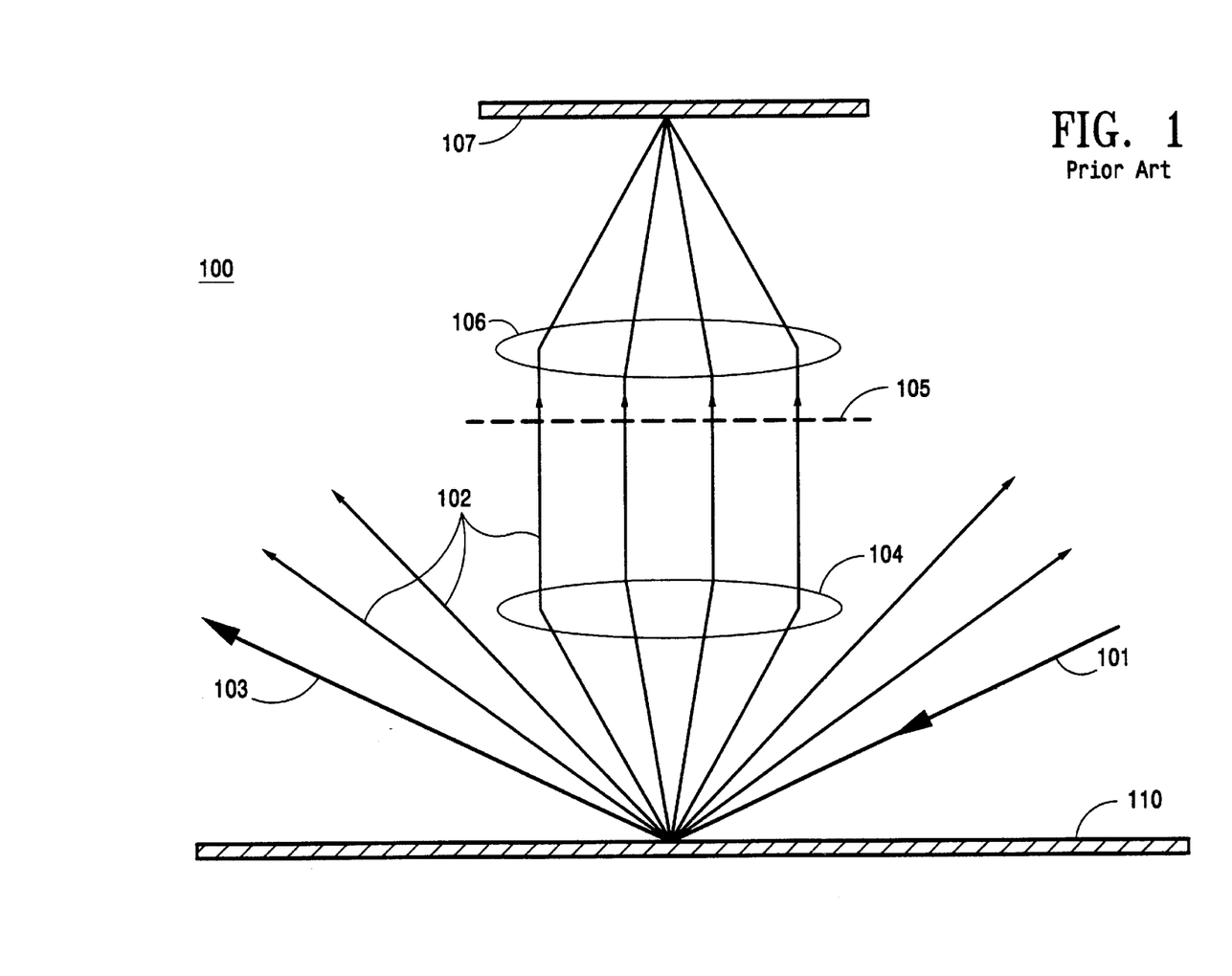
FIG. 1 is a diagram of a typical prior art Fourier filter used to block the diffraction orders created by an incident laser beam hitting the surface of a wafer.

FIG. 1 illustrates a conventional Fourier filter mechanism 100 for blocking the diffraction pattern created by repetitive patterning (not shown) on a wafer 110. A laser light beam 101 incident on wafer 110 produces diffraction orders 102 and a specular reflection 103. An objective lens 104 redirects diffracted light rays through an LCD-based or photographic-based filter positioned in Fourier plane 105 and through a second lens 106 to focus an image on an image sensor 107.

Figure 2A:
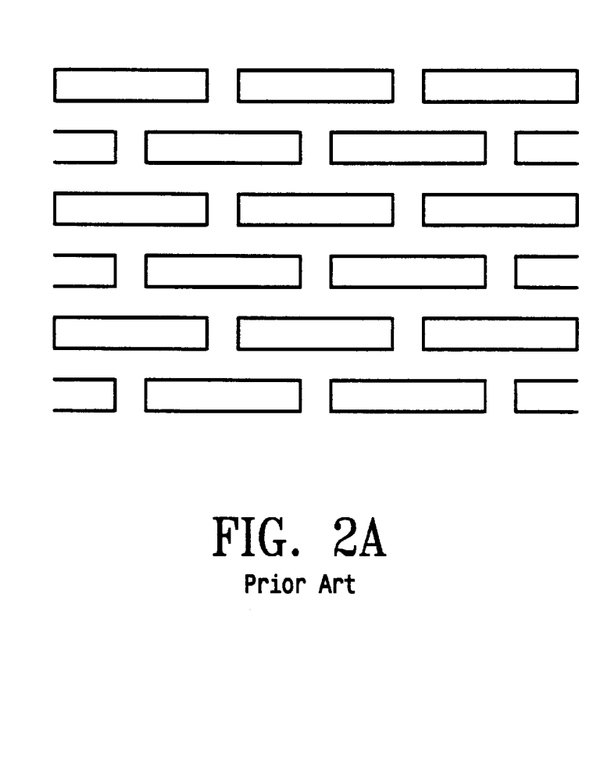
FIG. 2A is a diagram of a typical repeating array at the wafer image plane.
Figure 2B:
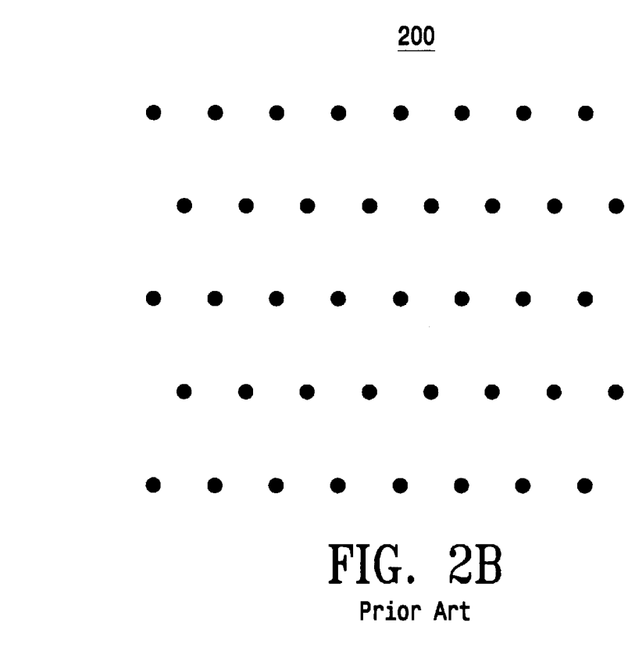
FIG. 2B is a typical Fourier spot pattern from the repeating array in FIG. 2A.

FIG. 2A shows a repeating array located at the wafer image plane and FIG. 2B shows the parallel and linear array of Fourier spots 200 produced by a collimated laser beam diffracted from the array.

By placing in the Fourier plane a blocking mechanism that occludes the diffraction spots, while leaving the rest of the Fourier plane unobstructed, it is possible to remove the repeating content without removing the non-repeating content (the defects) from the array area of the image. Removing the array repeating content is advantageous for two reasons:

First, the action of defining and comparing "identical" features on the wafer is inherently error-prone because the precise extent of the repeating pattern must be defined, and images must be precisely acquired and subtracted. If the repeating content is removed optically, the array area appears as an unpatterned wafer. The definition, image acquisition and comparison of adjacent repeating cells create optical clutter that is avoided when the repeating pattern is removed by the use of a Fourier filter.

Second, in order to perform the comparison described above, an accurate image of the repeating pattern is required, which means that the gain of the imaging system cannot be increased beyond the point where the image approaches saturation of the detector. This limits the size of defects that can be seen. If the imaging system gain were further increased, smaller defects might become detectable, but because the repeating pattern would be in saturation, the array features would be poorly resolved and comparison of adjacent repeating cells would result in large amounts of noise that would swamp the signal from the smaller defects. If the repeating pattern is removed optically using a Fourier filter, the system gain can be freely increased because the repeating image is removed before it reaches the detector. The Fourier filter therefore allows much larger gains to be used in array areas, and consequently much better defect sensitivity.

A practical Fourier filter must allow the quick detection of defects on semiconductor wafers, which means that the filter should not be susceptible to having the filter output affected by the normal vibrations present in a manufacturing environment. Therefore, what is needed is a low-cost Fourier filter mechanism in which the damping of vibrations requires a minimum of time and the damping means does not interfere with the utility of the Fourier filter itself.

SUMMARY OF THE INVENTION

The present invention is a Fourier filter mechanism with an array of blockages and at least two springs fabricated from a conductive material, to support the array of blockages. This Fourier filter mechanism is etched from a single sheet of spring material, such as beryllium copper. This provides an inexpensive and easy to manufacture filter, with very close tolerances achievable on the width of the blockages and close matching of the spring rates of the two springs. The close tolerances allow the blockage width to be kept very small so that optical efficiency is optimized, and allows the springs to be well matched for predictable, uniform, and repeatable stretching of the springs so that the blockages are evenly positioned.

DETAILED DESCRIPTION OF THE PREFERRED EMBODIMENT

The problem then, is how to effectively filter the diffraction spots in the Fourier plane. The goal is to have as high a contrast as possible between blocked and unblocked areas, and to have as high an optical efficiency as possible, i.e., to block as little of the plane as possible. Also of interest is that the inspection machine that uses this filter has two incident laser beams on the wafer, causing two sets of diffraction spots (see FIG. 3). An arrangement that blocks both of these diffraction patterns would be advantageous.

Figure 3:
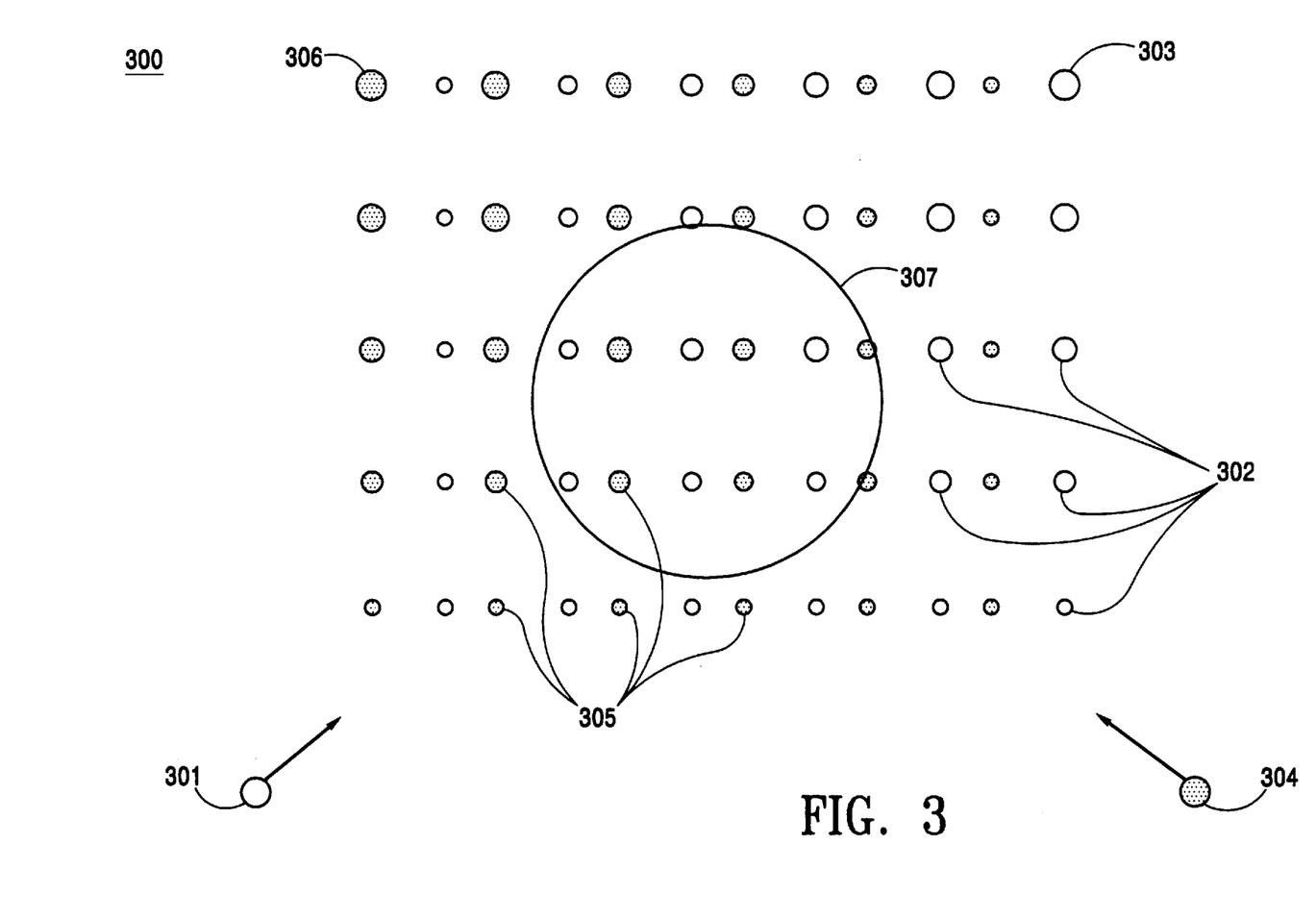
FIG. 3 is a diagram of the diffraction spots in the Fourier plane resulting from the use of two incident laser beams.

Referring now to FIG. 3, a diagram of the Fourier spot patterns 300 created from the array are shown as produced by the illumination of two laser beams, each providing a coherent, collimated beam of light. A beam 301 of incident laser light 'A' hits the wafer producing the 'A' diffraction orders 302 and 'A' specular reflection 303. A beam 304 of incident laser light 'B' hits the wafer producing the 'B' diffraction orders 305 and 'B' specular reflection 306. A Fourier plane aperture 307 is shown which samples the diffraction patterns for 'A' and 'B'.

Figure 4:
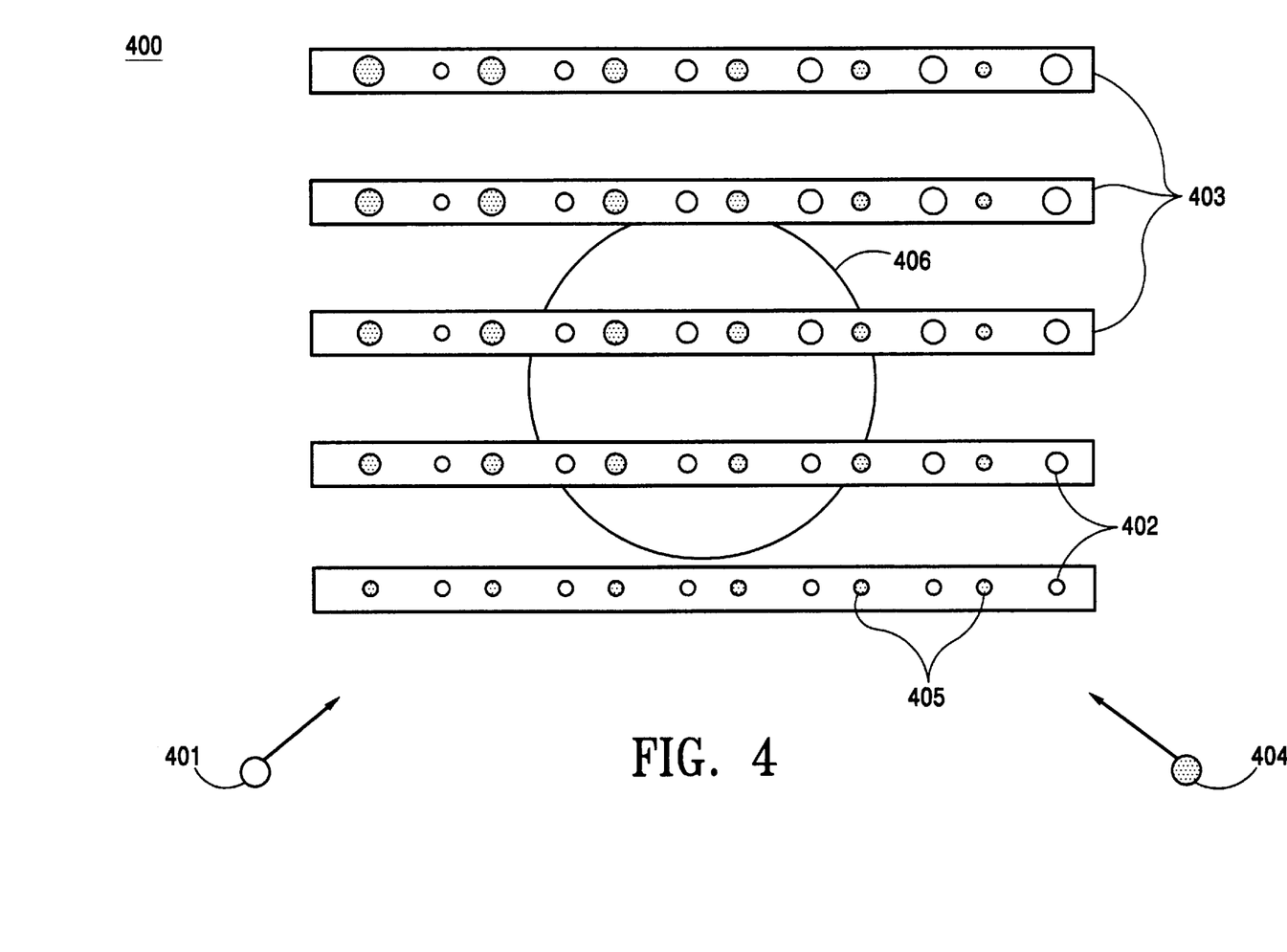
FIG. 4 is a diagram of the diffraction spots and filter blockages at the illumination elevation angle (theta)
Figure 5:
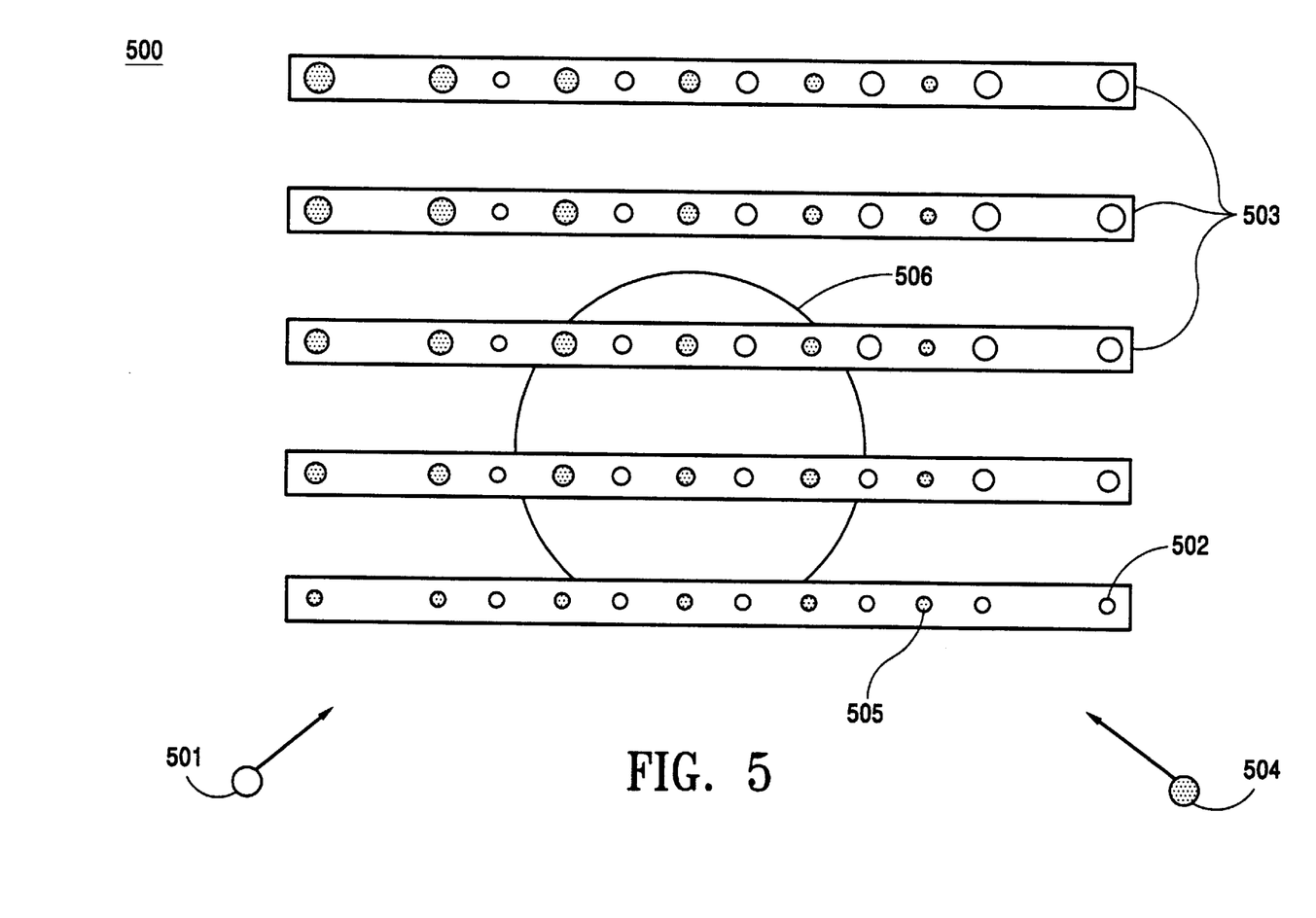
FIG. 5 is a diagram of the diffraction spots and filter blockages at the illumination elevation angle (theta plus nu)

Note: FIG. 3, FIG. 4 and FIG. 5 use size to represent intensity of the diffraction spots; the spots do not actually vary in size as shown, but they do vary in intensity. The two shadings are used to distinguish diffraction spots from the two incident beams.

Referring now to FIG. 4, a diagram of the Fourier spot patterns 400 created from the array is shown as produced by the illumination of two laser beams. FIG. 4 is a diagram of the diffraction spots and filter blockages at illumination elevation angle theta. A beam 401 of incident laser light 'A' hits the wafer producing the 'A' diffraction orders 402, which are blocked by wires or springs acting as filter blockages 403. A beam 404 of incident laser light 'B' hits the wafer producing the 'B' diffraction orders 405 also blocked by filter blockages 403. A Fourier plane aperture 406 is shown which samples the diffraction patterns for 'A' and 'B'.

Referring now to FIG. 5, a diagram of the Fourier spot patterns 500 created from the array is shown as produced by the illumination of two laser beams. FIG. 5 is a diagram of the diffraction spots and filter blockages at the illumination elevation angle (theta plus nu). A beam 501 of incident laser light 'A' hits the wafer producing the 'A' diffraction orders 502, which are blocked by wires or springs acting as filter blockages 503. A beam 504 of incident laser light 'B' hits the wafer producing the 'B' diffraction orders 505 also blocked by filter blockages 503. A Fourier plane aperture 506 is shown which samples the diffraction patterns for 'A' and 'B'.

One fundamental assumption behind the use of such Fourier filter mechanisms is that there is little vibration of the Fourier filter mechanism. The damping time constant for a Fourier filter mechanism can be quite large. The spring support for the filter by itself is a highly under-damped mechanism that tends to vibrate for a long time after it is shocked or moved. To avoid this problem, damping is normally provided by clamps, which physically contact and restrict the use of the Fourier filter. But without such damping, considerable time is needed to wait for any vibration to dampen to an insignificant amount. This time can add significant delay to the optical inspection of each wafer for defects and thereby greatly reduce the number of wafers that can be inspected in a fixed amount of time and thus increase the inspection cost.

Figure 6A:
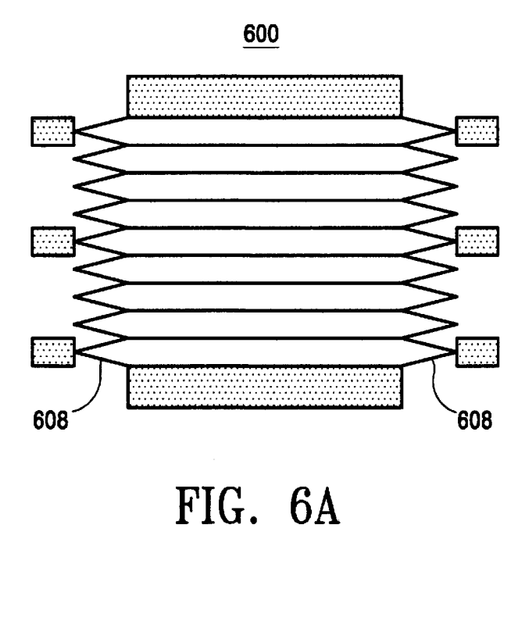
FIG. 6A is a diagram of one embodiment of a Fourier filter mechanism compressed.
Figure 6B:
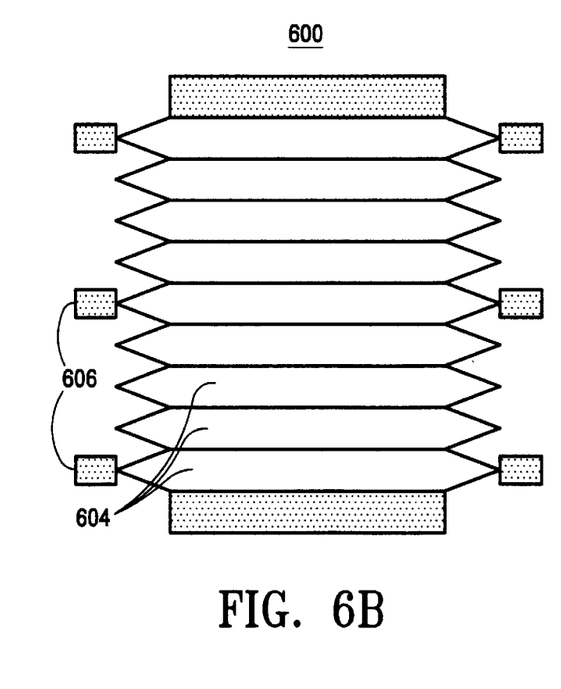
FIG. 6B is a diagram of the Fourier filter uncompressed.

The present invention uses a Fourier filter mechanism that produces an optical diffraction pattern for only non-repeating defects and which can be easily damped without clamps. FIG. 6A is a diagram of one embodiment of a Fourier filter mechanism 600 compressed and FIG. 6B is a diagram of the Fourier filter mechanism 600 uncompressed, showing damping tabs 606 for magnetically-induced eddy current damping. The filter blockages 604, the damping tabs 606 and the "Z-springs" 608 are shown at two pitch settings. Preferably, the Z-springs 608 should be more broadly spaced at the bottom than at the top when the Z-springs 608 are vertical, so that weight of the Z-spring will compress the Z-spring spacing on the bottom to be approximately equal to the Z-spring spacing on the top. The filter 604 itself is an array of blockages connected between two flat Z-springs 608. The spacing of the blockages changes as the springs are stretched or relaxed. This entire filter assembly is etched from a single sheet of spring material, such as beryllium-copper or stainless steel. This makes it possible to build an inexpensive and easy-to-manufacture filter, with very close tolerances achievable on the width of the blockages and close matching of the spring rates of the two Z-springs 608. The close tolerances allow the blockage width to be kept very small so that optical efficiency is optimized, and allows the Z-springs 608 to be well matched for predictable, uniform, and repeatable stretching of the springs so that the blockages are evenly positioned.

Figure 6C:
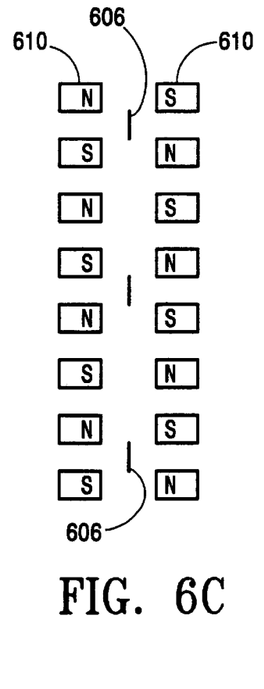
FIG. 6C is a folded side view of the tabs in FIG. 6B showing the relative position and spacing of the magnets and the tabs.

The Z-spring by itself is a highly under-damped mechanism that tends to vibrate for a long time after it is shocked or moved. The damping tabs 606 in FIG. 6A and FIG. 6B are simple rectangles of spring material that are placed in a magnetic field as part of the Fourier filter implementation. Even though rectangles are shown, any polygon shape would suffice. The preferred embodiment has the spacing of the magnets approximately equal to the size of the tabs, as seen in FIG. 6C. The damping tabs 606 are centered between magnets 610 that have approximately the same separation from each other and from the damping tabs 606 as the planar width of the damping tabs 606.

The magnetic field is created by arrays of small permanent magnets 610 of alternating polarity. When the tabs 606 move in the magnetic field, the magnetic flux through any electrical loops in the tabs changes, which induces eddy currents in the tabs 606, and the magnetic force vector caused by the eddy currents acts to damp out vibrations in the Z-spring 608. Thus, when this Fourier filter mechanism is subjected to normal environmental vibrations, the damping of the vibrations will be very fast so that the duration of the inspection time will not be substantially affected.

The tabs 606 must be formed of conductive material for the magnetically induced eddy currents to occur, and the beryllium-copper or stainless steel material of the spring 608 is conductive. The tabs 606 are etched as part of the same process that makes the springs 608 and blockages 604, and therefore come at virtually no additional cost. The etching is preferably done simultaneously on both sides of a conductive sheet. Laser cutting is another way in which to fabricate the springs, blockages and tabs. Preferably, the surface of the conductive material is oxidized after the etching or laser cutting process is completed. The purpose of oxidizing the surface of the filter is to make it black, but any other suitable method of blackening the surface of the filter could also be used.

The net effect of the tabs 606 and magnets 610 is that the time constant of the vibration is reduced by over an order of magnitude, from the order of ten seconds without damping to well under a second with damping. This damping is always beneficial and helps to damp out random vibrations from any source in the vicinity of the Fourier filter, as well as vibrations caused by deliberate filter adjustments. This damping technique is much more preferable than other methods of inhibiting the vibration, such as using clamps, which would restrict the use of the blockages and require physical contact by the clamps.

The rest of the filter amounts to motor and slide mechanisms to stretch the Z-springs 608 and to position the blockages and spring assembly as a whole. In one embodiment, this is accomplished with stepper motors and lead-screws.

Although the use of damping tabs is preferred, other methods of damping could be used, including placing a viscous liquid along the tracks near the edges of the spring, and allowing the viscous liquid to damp the spring's motion. Alternatively, a slight frictional coupling could be maintained between the edges of the spring and these tracks to damp the spring's motion. These methods could also be used in combination with one another, or in combination with other damping methods not disclosed herein. Although some form of damping is highly useful for a commercially successful device, damping is not needed if the device need not reach equilibrium in a short period of time, and if the device is isolated from other sources of vibration.

Figure 7:
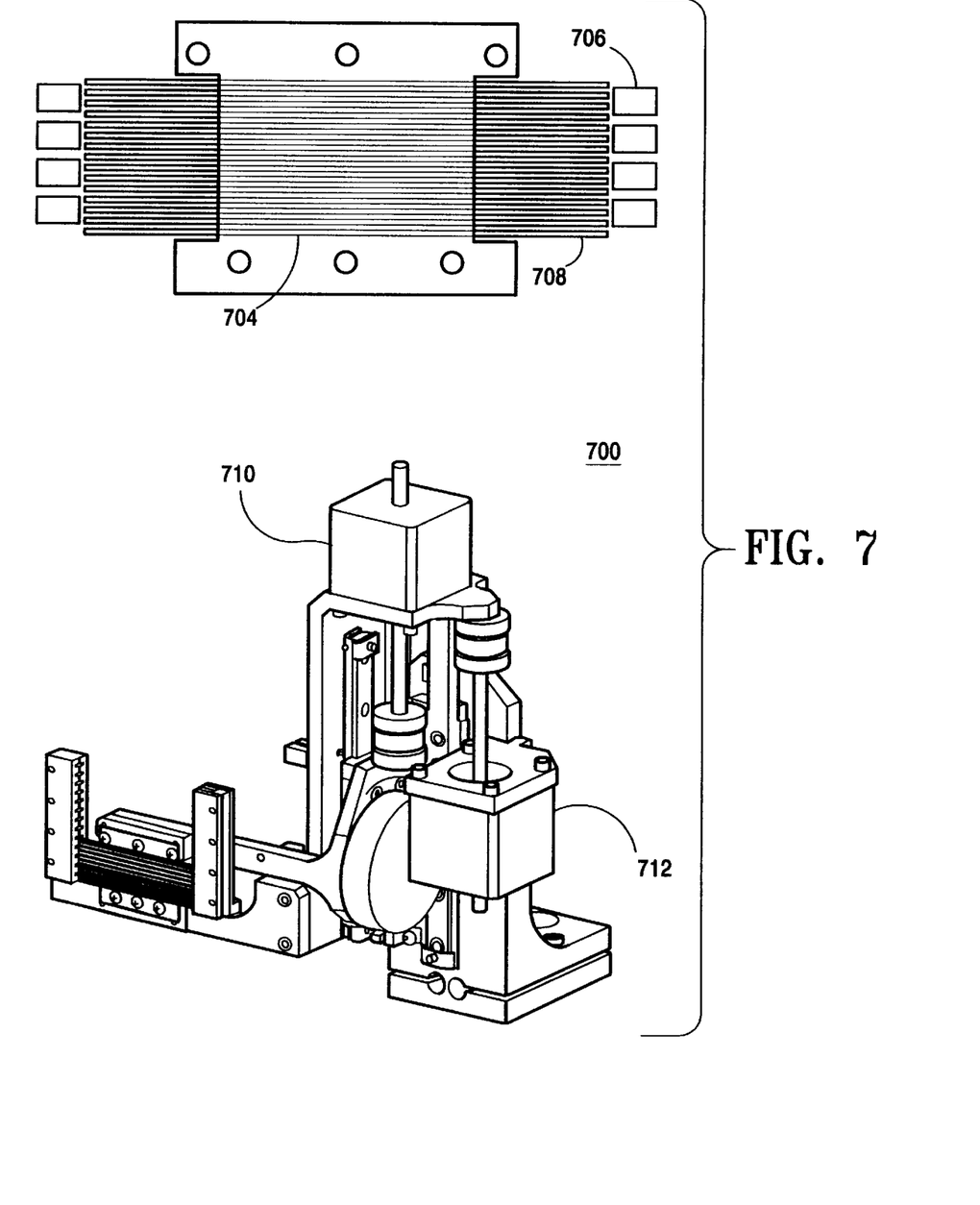
FIG. 7 shows an implementation of one embodiment of a Fourier filter in an inspection system.

FIG. 7 shows the implementation of filter blockages 704, the damping tabs 706 and the "Z-springs" 708 in an inspection system 700. The apparatus that adjusts the position of the filter includes two stepper motors. A first stepper motor 710 (in the center of FIG. 7) changes the compression of the spring or the relative spacing between the wires of the parallelogram. A second stepper motor 712 moves the entire filter as a unit without changing the compression. It can also be used to move the entire filter out of the optical path where Fourier filtering is not desired.

An alternate embodiment of a Fourier filtering mechanism uses mechanical wires to provide filtering in one dimension, because it has no distortion, infinite contrast, and can be adjusted without excessive cost and process complexity. The linear wires allow the diffraction spots from both incident laser beams to be blocked by a single filter. In one use of such filter blockages, the elevation angle of the laser beams is adjustable, which causes a diagonal translation of the Fourier patterns, but still allows the same filter blockages to cover both diffraction patterns (see FIG. 4 and FIG. 5).

Figure 8A:
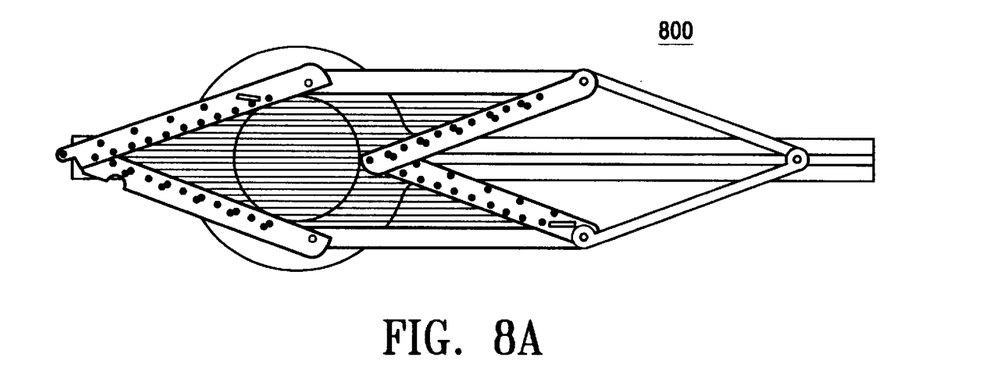
FIG. 8A and FIG. 8B show an alternative embodiment of a Fourier filter with a parallelogram mechanism with flexible wire strung between pins on the parallelogram arms.
Figure 8B:
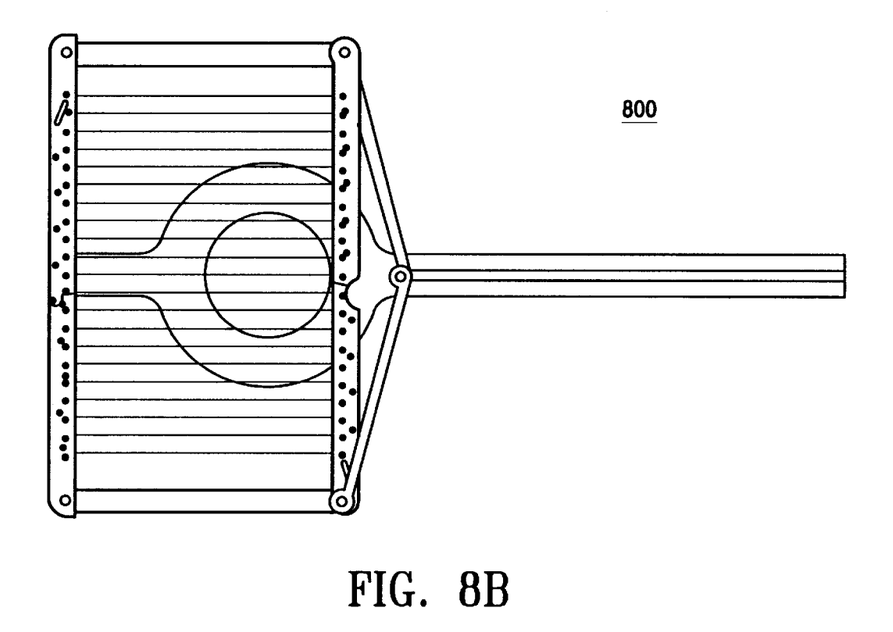
Figure 9:
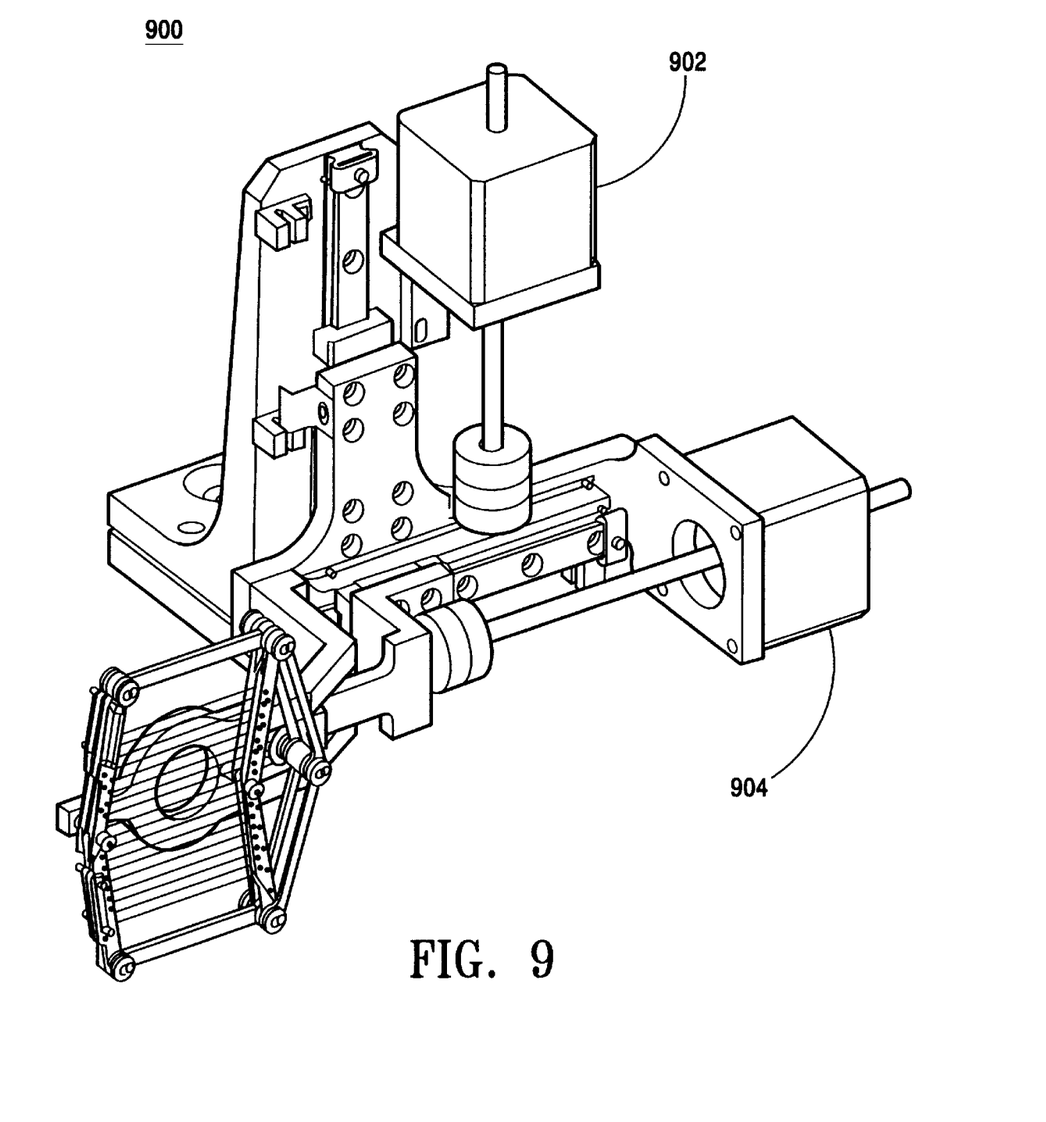
FIG. 9 shows an alternative embodiment of a Fourier filter in an inspection system.

FIG. 8A and FIG. 8B show the alternative embodiment of a Fourier filter using a folding parallelogram mechanism 800 with flexible wire strung on the parallelogram arms. FIG. 9 shows how this Fourier filter mechanism is used in an inspection system 900. The filter positioning apparatus includes two stepper motors. A first stepper motor 902 (on the left in FIG. 9) changes the compression of the spring or the relative spacing between the wires of the parallelogram. A second stepper motor 904 moves the entire filter as a unit without changing the compression. It can also be used to move the entire filter out of the optical path where Fourier filtering is not desired.

The spring is aligned with the spots when the Fourier filtering is desired. It can be aligned once, and then returned to the same settings for each new sample, or it can be aligned again with each new image. In the latter method, the total amount of incident light could be measured on the detector, and the spring's position would be adjusted until that amount was at a minimum (corresponding to the position at which the diffraction spots caused by repeating images are blocked).

Those skilled in the art will recognize that the Fourier filter mechanism described above can be implemented with a variety of filters, depending on the application. Therefore, the present invention is limited only by the following claims.

What is claimed is:

1. A Fourier filtering mechanism for detecting defects in repetitive features on semiconductor wafers, comprising:
   an array of substantially coplanar adjustable blockages;
   a plurality of springs supporting the array of blockages, said array of blockages and said plurality of springs being fabricated by etching a sheet of conductive spring material;
   a plurality of positioning devices for stretching said plurality of springs and positioning said array of blockages; and
   a plurality of damping tabs fabricated from a conductive material, and positioned in proximity to an array of permanent magnets, for damping vibration of said springs.

2. The Fourier filtering mechanism of claim 1 further comprising a plurality of damping tabs fabricated from a conductive material, positioned in proximity to an array of permanent magnets.

3. A Fourier filtering mechanism for inspecting for defects in repetitive features in semiconductor structures, comprising:
   an array of substantially coplanar, mechanically adjustable blockages;
   a plurality of springs supporting the array of blockages;
   a plurality of damping tabs, attached to the plurality of springs, for damping vibration of the plurality of springs; the array of blockages, the plurality of springs and the plurality of damping tabs being fabricated from a conductive material which has been blackened; and
   an array of permanent magnets of alternating polarities, in proximity to, and for inducing eddy currents in, said plurality of damping tabs.

4. The Fourier filtering mechanism of claim 3, further comprising:
   at least one source of substantially coherent and collimated light.

5. The Fourier filtering mechanism of claim 3, further comprising:
   at least one stepper motor to stretch and position the array of blockages; and
   at least one lead-screw to position the array of blockages.

6. A method of using an array of blockages as a Fourier filtering mechanism for inspecting for defects in repetitive features in semiconductor devices, comprising the steps of:
   fabricating an array of blockages;
   illuminating an area of a semiconductor wafer with a means for producing substantially collimated light;
   positioning the array of blockages between the semiconductor wafer and an image sensor in a Fourier plane to block diffraction orders produced by the illuminating step; and
   positioning the semiconductor wafer relative to the position of the illuminating means so that different die patterns on the semiconductor wafer occupy the illuminated area.

7. The method of claim 6 wherein said step of fabricating etches a sheet of spring material.

8. The method of claim 6 wherein said means for producing substantially collimated light comprises at least one laser source.

9. The method of claim 8 wherein said step of illuminating uses collimated light beams from two laser sources.

10. The method of claim 9 wherein said step of illuminating produces a diffraction order from said semiconductor wafer and a specular reflection from said semiconductor wafer, and said blockages effectively block the diffraction orders for both collimated light beams.

11. A Fourier filtering mechanism for detecting defects in repetitive features on a semiconductor wafer, comprising:

an array of substantially coplanar adjustable blockages;

damping supports coupled to said adjustable blockages to minimize the effects of vibration;

a source of substantially collimated light for illuminating an area of a semiconductor wafer;

an image sensor for receiving said collimated light; and positioning devices for positioning said array of blockages and said damping supports in a Fourier plane between the semiconductor wafer and the image sensor to block diffraction orders produced by the collimated light impinging on said semiconductor wafer.

12. The Fourier filtering mechanism of claim 11 wherein said blockages produce an optical diffraction pattern only for non-repeating defects on said semiconductor wafer.

13. The Fourier filtering mechanism of claim 12 wherein said damping supports comprise a plurality of springs supporting the array of blockages.

14. The Fourier filtering mechanism of claim 13 wherein said blockages are fabricated from a single sheet of spring material.

15. The Fourier filtering mechanism of claim 12 wherein said damping supports comprise a plurality of conductive tabs disposed in a magnetic field to generate eddy currents in said tabs and thereby damp vibrations in said array of blockages.

16. The Fourier filtering mechanism of claim 12 wherein said damping supports comprise a viscous fluid disposed along the path of movement of said blockages to damp vibration in said array of blockages.

17. The Fourier filtering mechanism of claim 12 wherein said blockages comprise flexible mechanical wires for providing filtering in one dimension.

18. The Fourier filtering mechanism of claim 12 wherein said blockages comprise a folding parallelogram with flexible wire strung on the arms of said parallelogram.

19. The Fourier filtering mechanism of claim 18 further including a first stepper motor for changing the relative spacing of the wires of said parallelogram, and a second stepper motor for moving said parallelogram as a unit.

20. A Fourier filtering mechanism for inspecting for defects in repetitive features in semiconductor structures, comprising:

an array of substantially coplanar adjustable mechanical blockages in a Fourier plane for use as a Fourier filter; and a parallelogram frame supporting the array of blockages, wherein the spacing of the blockages can be adjusted by altering the shape of the parallelogram.

21. A method of etching a conductive sheet having a first side and a second side to create a Fourier filtering mechanism for detecting defects in repetitive features on semiconductor wafers, comprising the steps of:

masking out an array of blockages and a plurality of springs and damping tabs on a first side of a sheet of conductive material;

masking out an array of blockages and a plurality of springs and damping tabs on a second side of the sheet of conductive material;

etching out an array of blockages and a plurality of springs and damping tabs from the sheet of conductive material; and blackening at least part of the Fourier filtering mechanism after it is etched.

* * * * *